United States Patent [19]

Brewer et al.

[11] Patent Number: 4,634,707
[45] Date of Patent: Jan. 6, 1987

[54] 5-PYRIMIDINECARBOXAMIDES AND TREATMENT OF LEUKEMIA AND TUMORS THEREWITH

[75] Inventors: Arthur D. Brewer, Puslinch, Canada; John A. Minatelli, Watertown, Conn.

[73] Assignees: Uniroyal Chemical Company, Middlebury, Conn.; Uniroyal Ltd., Don Mills, Canada

[21] Appl. No.: 699,776

[22] Filed: Feb. 8, 1985

Related U.S. Application Data

[63] Continuation-in-part of Ser. No. 665,201, Oct. 26, 1984, abandoned, and Ser. No. 562,693, Dec. 19, 1983, abandoned.

[30] Foreign Application Priority Data

Dec. 18, 1984 [BE] Belgium ............................ 0/214.179

[51] Int. Cl.$^4$ .................. A61K 31/515; C07D 239/66; C07D 239/68

[52] U.S. Cl. ...................................... 514/270; 544/301

[58] Field of Search .................... 544/301; 536/23; 514/269, 270

[56] References Cited

U.S. PATENT DOCUMENTS

| | | | |
|---|---|---|---|
| 3,961,061 | 6/1976 | Kramer et al. | 544/301 |
| 4,229,454 | 10/1980 | Beriger | 514/270 |
| 4,283,444 | 8/1981 | de Sousa et al. | 544/301 |
| 4,349,552 | 9/1982 | Takaya et al. | 544/313 |
| 4,410,524 | 10/1983 | Murdock | 544/72 |

FOREIGN PATENT DOCUMENTS

| | | |
|---|---|---|
| 825150 | 8/1975 | Belgium . |
| 10941 | 5/1980 | European Pat. Off. . |
| 74335 | 3/1983 | European Pat. Off. . |
| 105029 | 4/1984 | European Pat. Off. . |
| 105030 | 4/1984 | European Pat. Off. . |
| 2405732 | 8/1975 | Fed. Rep. of Germany . |
| 2719733 | 5/1977 | Fed. Rep. of Germany . |
| 2936457 | 3/1980 | Fed. Rep. of Germany . |
| 39-1445 | 2/1964 | Japan .................................. 544/301 |
| 602664 | 7/1978 | Switzerland . |
| 614944 | 12/1979 | Switzerland . |

OTHER PUBLICATIONS

Chem. & Pharm. Bulletin, vol. 8, 1960, pp. 1021–1028.
C.A. 56: 5344h.
C.A. 68:67566m.
C.A. 68: 49548c.
C.A. 68: 39560m.

(List continued on next page.)

Primary Examiner—Donald G. Daus
Assistant Examiner—Stephen M. Kapner
Attorney, Agent, or Firm—John A. Shedden

[57] ABSTRACT

Novel 5-pyrimidinecarboxamides useful for regressing or inhibiting the growth of leukemia and tumors in mammals. The compounds have the formula:

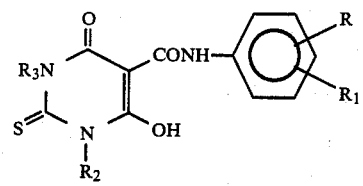

wherein:
R is hydrogen, 2- or 3-halo, 4-fluoro, 2-methyl, 2- or 4-alkoxy, or 2- or 4-trifluoromethyl, and $R_1$ is hydrogen; or
R is 2-fluoro and $R_1$ is 4-fluoro; or
R is 2-methoxy and $R_1$ is 5-methyl; and
$R_2$ and $R_3$ are hydrogen atoms or carbohydrate residues; and, with the exception of the compound wherein R is 4-methoxy and $R_1$ is hydrogen, the pharmacologically acceptable acid-addition salts thereof.

24 Claims, 1 Drawing Figure

OTHER PUBLICATIONS

C.A. 78: 124531d.
C.A. 86: 134902e.
C.A. 88: 46386a.
C.A. 93: 181034c.
C.A. 93: 8205m.
C.A. 94: 47313k.
C.A. 98: 34595m.
Diss. Pharm. Et. Pharmolog., 1966, XVIII, 1, 31.
Chem. Ber., 106, 312–316 (1973).
J. Soc. Dyers Colour, 99(4), pp. 118–121 (1983).
J. Org. Chem., 44, No. 26, 1979, pp. 4877–4880.
J. Heterocycl. Chem., 9(4), pp. 955–958 (1972).
Brewer et al., *Biochemical Pharmacology*, vol. 34, No. 11, pp. 2047–2050, 1985.
Busch et al., eds., "Effects of Drugs on the Cell Nucleus", vol. 1, pp. 275–299, ©1979, Academic Press Inc.
Robins, R. K., "Synthetic Antivoral Agents", in *Chem. & Eng. News*, Jan. 27, 1986, pp. 28–40.
"In Vivo Cancer Models", U.S. Dept. of Health and Human Services, National Institutes of Health Pub. #84–2635, Feb. 1984.

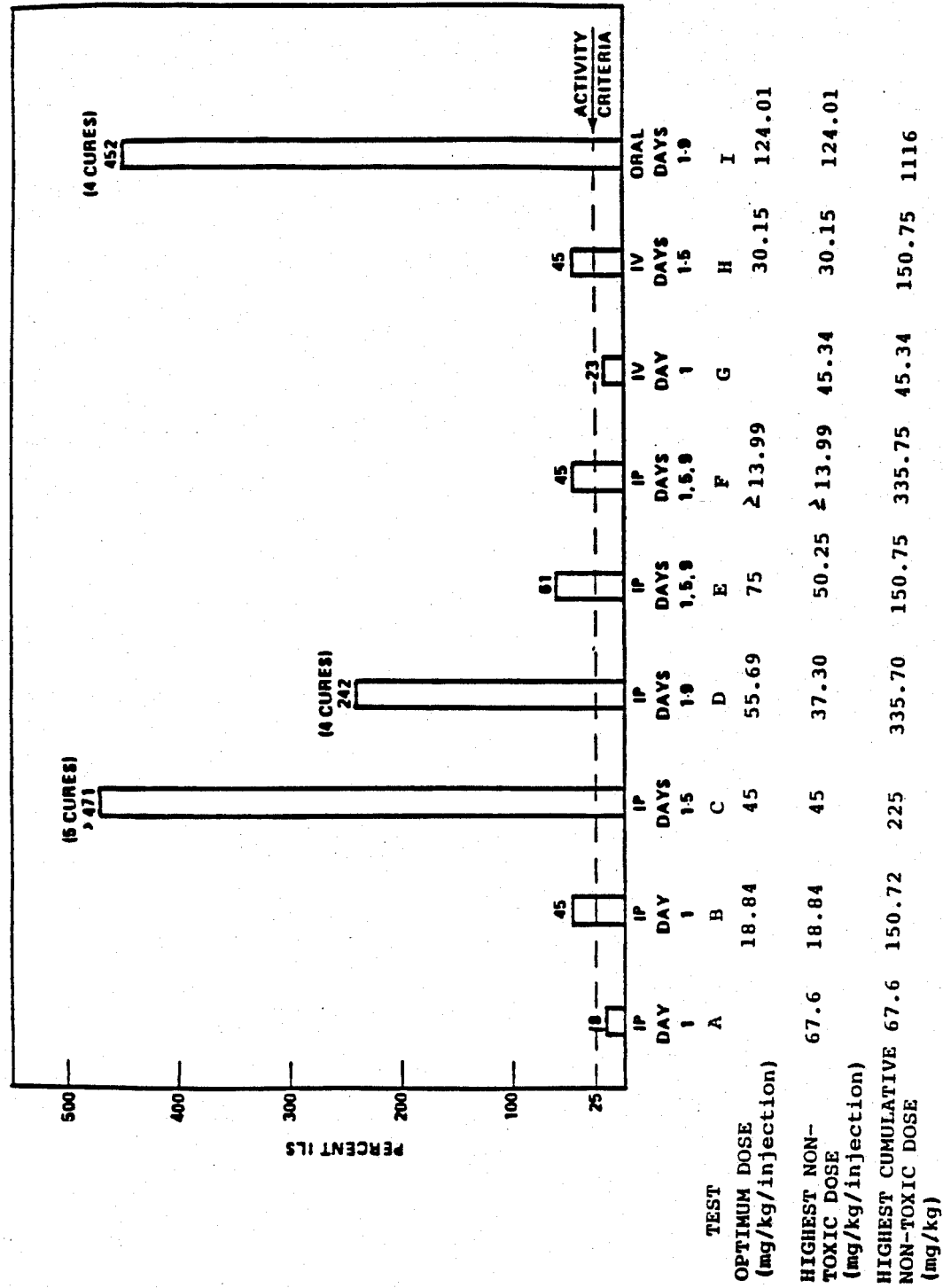

5-PYRIMIDINECARBOXAMIDES AND TREATMENT OF LEUKEMIA AND TUMORS THEREWITH

CROSS-REFERENCE TO RELATED APPLICATION

This is a continuation-in-part of copending applications Ser. No. 562,693 filed Dec. 19, 1983, now abandoned and Ser. No. 665,201 filed Oct. 26, 1984, now abandoned the disclosures of which are incorporated herein.

TECHNICAL FIELD

This invention relates to new 5-pyrimidinecarboxamides, and the pharmacologically acceptable addition salts and nucleosides thereof. More particularly, the invention relates to new 5-pyrimidinecarboxamide derivatives which have anti-leukemia and anti-tumor activity, to pharmaceutical compositions containing such derivatives as the therapeutically effective constituents thereof, and to a method utilizing the same for inducing the regression of leukemia and/or the inhibition of growth of tumors in mammals.

BACKGROUND ART 5-pyrimidinecarboxamides, and particularly 5-carboxamides of barbituric acid, have previously been described as potential anti-cancer agents. Thus, Takeda Pharmaceutical Industries' Japanese Patent Publication No. 1,445/64, published on Feb. 14, 1964, suggests the use of compounds of the formula:

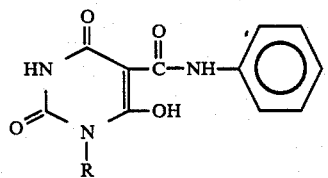

(I)

i.e., 5-phenylcarbamoylbarbituric acid (wherein R is hydrogen) and 1-substituted-phenylcarbamoylbarbituric acids (wherein R is alkyl or phenyl), for such purpose. When subjected to in vivo testing on Ehrlich Ascites carcinoma in mice the unsubstituted compound, but neither of its 1-methyl or 1-phenyl-substituted derivatives, exhibited anti-tumor activity. Chem. & Pharm. Bull. (Tokyo) 8, 1021-1028 (1960).

Analogs of similar barbituric acid derivatives have also been described in the literature. Thus, N-substituted-2-amidocarbonylthiobarbituric acids of the formula:

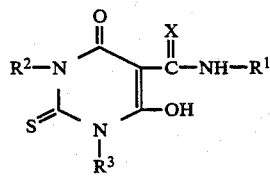

(II)

wherein $R^1$ is alkyl, alkenyl, various substituted alkyl, alkenyl or carbonyl, or optionally substituted aryl or aralkyl, $R^2$ and $R^3$ each independently is alkyl, alkenyl, cycloalkyl, aryl, aralkyl or hydrogen, provided that not more than one of $R^2$ and $R^3$ is hydrogen, and X is oxygen or sulfur, are disclosed in Bayer AG German Offen. No. 24 05 732 and in Kramer et al., U.S. Pat. No. 3,961,061 granted on June 1, 1976. These thiobarbituric acid derivatives are described as possessing insecticidal, acaricidal, fungicidal and bactericidal properties.

Other 5-carboxamido-substituted thiobarbituric acids such as:

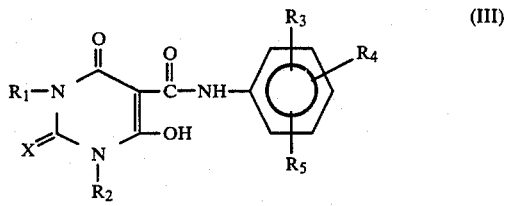

(III)

wherein X is oxygen or sulfur, $R_1$ and $R_2$ may each be alkyl, alkenyl, benzyl or unsubstituted or substituted phenyl, $R_3$ may be halogen, nitro or trihalomethyl, $R_4$ is hydrogen, halogen or trihalomethyl, and $R_5$ is hydrogen, halogen, methyl or methoxy, are also described in the patent literature. Such compounds are disclosed in Ciba-Geigy European Patent Publication No. 74,335 and in De Sousa et al., U.S. Pat. No. 4,283,444 granted on Aug. 11, 1981, as useful for protecting keratinous material, especially wool, from insect attack.

It is among the objects of the present invention to provide a new class of 5-pyrimidinecarboxamides, in particular a new group of 5-carboxamide-2-thiobarbituric acid derivatives, which are useful anti-leukemia and anti-tumor agents, as well as pharmaceutical compositions and therapeutic methods for utilizing the same. Other objects and advantages of the invention will be apparent from the following detailed description of preferred embodiments thereof.

SUMMARY OF THE INVENTION

The novel 5-pyrimidinecarboxamides of the present invention are 5-carboxamide-2-thiobarbituric acid derivatives of the formula:

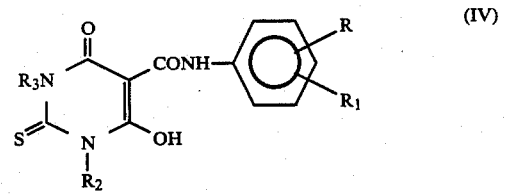

(IV)

wherein
R is hydrogen, 2 or 3-halo, 2-methyl, 4-fluoro, 4-($C_1$-$C_6$ alkoxyl), 2 or 4-trifluoromethyl, or hydroxyl, and $R_1$ is hydrogen;
or R is 2-fluoro and $R_1$ is 4-fluoro;
or R is 2-methoxy and $R_1$ is 5-methyl; and
$R_2$ and $R_3$ are hydrogen atoms or carbohydrate residues; and the pharmacologically acceptable addition salts thereof.

When $R_2$ is hydrogen, addition salts may be formed with a variety of pharmacologically acceptable organic and inorganic salt-forming reagents. Addition salts may thus be formed by admixture of the organic acid with one equivalent of a base, e.g., an organic amine such as triethylamine or N-methyl glucamine, and inorganic cations such as sodium, potassium or the like. The addition salts of the organic acids of the invention are, in general, crystalline solids which are relatively insoluble in both polar solvents such as water, methanol and ethanol and non-polar organic solvents such as diethyl ether, benzene, toluene and the like. They are somewhat soluble in aprotic solvents such as dimethylformamide and dimethylsulfoxide.

On the other hand, when $R_2$ is a carbohydrate residue it may be furanosyl (e.g., ribofuranosyl), pyranosyl (e.g., arabinopyranosyl, glucopyranosyl, or gelactopyranosyl), their deoxy derivatives, or their aliphatic analogs (e.g., hydroxyalkoxyalkyl or polyhydroxyalkyl groups having from 2 to 12 carbon atoms in each of the alkoxy and alkyl moieties thereof, such as 2-hydroxyethoxymethyl or 2,3-dihydroxypropyl. As used herein, the term "carbohydrate residue" is intended to refer to those cyclic and acyclic groups which form pyrimidine nucleosides or the pseudo nucleosides, e.g., materials including both the cyclic and acyclic groups specified hereinabove.

The 5-carboxamide-2-thiobarbituric acid derivatives of the invention can exist in the form illustrated in Formula IV or in any of its tautomeric forms. For ease of understanding, the compounds of the invention will only be illustrated herein in the form shown in Formula IV but will be understood to embrace the tautomers thereof, or tautomeric mixtures.

The novel 5-carboxamide-2-thiobarbituric acid derivatives of the invention may be readily prepared by reacting 2-thiobarbituric acid with phenylisocyanate or an appropriate substituted phenylisocyanate, in the presence of a solvent or dispersing medium such as dimethylsulfoxide, pyridine, dimethylformamide, N-methylpyrrolidone, dimethylacetamide, sulfolane, tetrahydrothiophene oxide, acetonitrile, or a tertiary amine such as triethylamine. The molar proportions of the 2-thiobarbituric acid to the phenylisocyanate reactant may range from about 2:1 to 1:2, and are preferably from about 1.1:1 to 1:1.1, stoichiometric proportions generally sufficing. The reaction may be carried out at temperatures varying from about 0° to 200° C., usually at from about 24° to 160° C.; in most cases, the reaction proceeds quite well at temperatures of from about 80° to 100° C. Formation of the 5-carboxamide derivatives is substantially complete within reaction periods varying from about ½ to 6, and usually from about 2 to 4, hours.

Alternatively, the carboxamides may be prepared by other routes. For example, thiourea may be reacted with appropriately substituted 2-benzoylamino propanedioic diesters, and the resulting products separated and recovered. Other syntheses of the 5-carboxamide-2-thiobarbituric acid derivatives will readily occur to those skilled in the art.

The novel compounds of the invention are cytotoxic agents useful to induce the regression of blood malignancies such as leukemia, as well as to inhibit the growth of solid and non-solid tumors. They may be used alone or in combination with other chemotherapeutic agents active for these purposes. As used herein, the terms "regression" and "inhibition" comprehend arresting or retarding the growth of the malignancy or other manifestation of the disease, as compared with the course of the disease in the absence of treatment.

Administration of the novel 5-carboxamido-2-thiobarbituric acid derivatives to mice in amounts ranging from about 12–200 mg./kg., preferably from about 25–100 mg./kg., of body weight has been found effective to induce the regression of leukemia and to inhibit the growth of tumors. The interrelationship of dosages for mammals of other sizes and species is described by Freireich, E. J., et al., Quantitative Comparison of Toxicity of Anti-cancer Agents in Mouse, Rat, Hamster, Dog. Monkey and Man, Cancer Chemotherapy, Reg. 50, No. 4,219-244, May 1966.

The dosage level may, of course, be adjusted to provide optimum therapeutic response. For example, several divided doses may be administered daily, or the dose may be proportionally reduced, as indicated by the exigencies of the therapuetic situation.

The active compounds may suitably be administered parenterally, intraperitoneally, intravenously or orally. Solutions or dispersions of the active compounds can be prepared in water, suitably mixed with a surfactant such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. For such uses the form must be sterile and must be fluid to the extent necessary to provide easy syringability. It must be stable under the conditions of manufacture and storage and must be preserved against the contaminating action of microorganisms such as baceteria and fungi.

The carrier can be a solvent or dispersing medium containing, for example, water, ethanol, a polyol (for example, glycerol, propylene glycol, and liquid polyethylene glycol, or the like), suitable mixtures thereof, and vegetable oils. The proper fluidity can be maintained, for example, by the use of a coating such as lecithin, by the maintenance of the required particle size in the case of a dispersion, and by the use of surfactants. Prevention of the action of microorganisms can be insured by various anti-bacterial and antifungal agents, for example, paraben, chlorobutanol, phenol, sorbic acid, thimerosal, or the like. In many cases it may be preferable to include isotonic agents, for example sugars or sodium chloride, in the dosage form. Prolonged absorption of the injectable formulations can be brought about by incorporating agents delaying absorption, for example, aluminum monostearate and gelatin, therein.

Steile injectable solutions are prepared by incorporating the active compound in the appropriate solvent, in admixture with various of the other ingredients enumerated above, as required, followed by filtered sterilization. Generally, dispersions are prepared by incorporating the sterilized active ingredient in a sterile vehicle which contains the dispersing medium and any other required ingredients. When, on the other hand, sterile powders are used to prepare sterile injectable solutions, it is preferred to subject a sterile, filtered solution of the desired ingredients to vacuum drying or freeze-drying, yielding a powder of the active ingredient plus any additional desired ingredients.

As used herein, "pharmaceutically acceptable, substantially nontoxic carrier or excipient" includes solvents, dispersing media, coatings, antibacterial and antifungal agents, isotonic and absorption delaying agents and the like. The use of such media and agents as carriers or excipients for pharmaceutically active substances is well known in the art. Except insofar as any conventional medium or agent is incompatible with the active ingredient or toxic, its use in the therapeutic formulations of the invention is contemplated. Supplementary active ingredients can also be incorporated in the therapeutic compositions.

It may be advantageous to formulate the compositions of the invention in unit dosage forms for ease of administration and uniformity of dosage. A unit dosage form, as used herein, refers to a physically discrete unit suitable for use as a unitary dosage for the mammalian subjects to be treated; each unit contains a predetermined quantity of active material calculated to produce the desired therapeutic effect, in association with the required pharmaceutically acceptable carrier. Specifications for unit dosage forms are dictated by and directly depend on (a) the unique characteristics of the active material and the particular therapeutic effect to be achieved, and (b) the limitations inherent in the art of compounding such an active material for the treatment of disease in living subjects having a diseased condition, without excessive cytotoxic side effects.

Regression of leukemia and inhibition of tumor growth may be attained, for example, by the use of daily dosing for up to 5 to 10 days, or longer. Multiple dosing, or dosing on any desired periodic basis, may also be utilized. The therapeutically active ingredient is thus administered in amounts sufficient to aid regression and inhibition of further growth of the leukemia or tumor, in the absence of excessive deleterious side effects of a cytotoxic nature.

BRIEF DESCRIPTION OF THE DRAWING

The accompanying drawing is a graph showing the effects of treatment schedule and route of administration of one of the compounds of the invention in the regression of L1210 lymphoid leukemia.

BEST MODE FOR CARRYING OUT THE INVENTION

Preferred among the 5-carboxamido-2-thiobarbituric acid derivatives hereof are compounds within the scope of Formula IV above, wherein R and $R_1$ are hydrogen (Example 1 below), R is 2-chloro and $R_1$ is hydrogen (Example 2), R is 2-methyl and $R_1$ is hydrogen (Example 3), R is 3-fluoro and $R_1$ is hydrogen (Example 4), R is 4-fluoro and $R_1$ is hydrogen (Example 5), R is 4-methoxy and $R_1$ is hydrogen (Example 6), R is 4-ethoxy and $R_1$ is hydrogen (Example 7), R is 2-fluoro and $R_1$ is hydrogen (Example 8), R is 2-fluoro and $R_1$ is 4-fluoro (Example 9), and R is 2-methoxy and $R_1$ is 5-methyl (Example 10). Particularly preferred is the compound of Example 1, viz., 1,2,3,4-tetrahydro-6-hydroxy-4-oxo-N-phenyl-2-thioxo-5-pyrimidinecarboxamide;

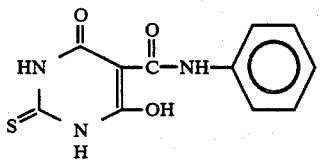
(V)

The invention will be described in greater detail in connection with the following specific examples illustrating the preparation and pharmacological testing of preferred embodiments of the compounds of the invention:

EXAMPLE 1

Preparation of 1,2,3,4-tetrahydro-6-hydroxy-4-oxo-N-phenyl-2-thioxo-5-pyrimidinecarboxamide A. Reaction of Thiobarbituric Acid with Phenylisocyanate 14.4 g of 2-thiobarbituric acid (which may, alternatively, be named dihydro-2-thioxo-4,6-(1H,5H)-pyrimidinedione or 4,6-dihydroxy-2-mercaptopyrimidine) and 11.9 g of phenylisocyanate were dissolved in dry pyridine (100 ml.). The solution was heated with stirring, and maintained at 75°–85° C. for about 4 hours. Upon cooling, an orange-colored solid precipitated out which was isolated, washed with about 25 ml dimethylformamide and dried.

Yield: 16.8 g (64%) NMR (DMSO) 7.1–8.0δ (multiplet; integral 5); 11.4δ (singlet, 1); 12.0 –13.7δ (broad diffuse peak, 3).

An elemental analysis for $C_{11}H_9N_3O_3S$ gave the following results:

|   | Calculated | Found (%) |
| --- | --- | --- |
| C | 50.19 | 50.30 |
| H | 3.45 | 4.02 |
| N | 15.96 | 15.75 |

| Mass spectrometric analysis was as follows: | | |
| --- | --- | --- |
|  | Calculated | Found |
| M/E = | 263 | 263 |

The compound decomposed at 310° C.+. The structure was further confirmed by an X-ray crystallographic study of the triethylammonium salt.

B. Reaction of Thiourea with Carboxanilidomalonate

Thiourea (1.5 g) was intimately mixed with carboxanilidomalonate, viz.,

(3.6 g), and very gently heated in a small flask in an oil bath. At about 115° C. the reaction mixture became semi-liquid with a solid residue remaining in the bottom of the flask. At about 150° C. the reaction mixture began to thicken, a volatile material being evolved. The reaction mixture was heated to 180°, left at that temperature for ½ hour, and then cooled. A khaki, ochre colored powder product was thus produced.

The product was washed with ethanol and dried (1.8 g). The mass spectrum was consistent with the product of Example 1A. Molecular Weight—263; 171 (pyrimidine fragment); 93 (aniline fragment).

EXAMPLE 2

Preparation of N-(2-chlorophenyl)-1,2,3,4-tetrahydro-6-hydroxy-4-oxo-2-thioxo-5-pyrimidinecarboxamide 2-thiobarbituric acid (14.4 g) was carefully dried, finely powdered and suspended in dry pyridine (100 ml). The suspension was warmed with stirring to about 50°, and 2-chlorophenylisocyanate (15.35 g) added. Much of the suspension went into solution. The mixture was stirred at 75°–85° for 4 hours and left overnight at room temperature.

The pyrimidinecarboxamide was collected as a purple powder; it was washed with a small quantity of pyridine, which removed most of the color, resuspended and triturated in 100% ethanol, collected and dried. Yield 23 g (77%), off-white powder, no sharp melting point (decomposes above 250° C.). NMR (DMSO) 7.1–8.3$\delta$ (multiplet; integral 4); 11.8$\delta$ (singlet, 1): 11.7–13.0$\delta$ (broad diffuse peak, 3).

Mass Spectrum 299–297 (molecular ion, chlorine isotopes); 171 (pyrimidine carbonyl fragment); 129–127 (o-chloroaniline, chlorine isotopes).

EXAMPLE 3

Preparation of 1,2,3,4-tetrahydro-6-hydroxy-N-(2-methylphenyl)-4-oxo-2-thioxo-5-pyrimidine-carboxamide The procedure described in Example 2 was repeated, reacting 2-thiobarbituric acid and 2-methylphenylisocyanate to give the pyrimidinecarboxamide as a tan powder, mp 250° (dec.); NMR (DMSO), 2.3$\delta$, singlet, integral 3; 7.15–8.00$\delta$ multiplet, 4; 11.4$\delta$ singlet, 1; 12.0–13.7$\delta$, broad diffuse peak, 3. Mass Spectrum 277, 171, 107.

EXAMPLE 4

Preparation of N-(3-fluorophenyl)-1,2,3,4-tetrahydro-6-hydroxy-4-oxo-2-thioxo-5-pyrmidinecarboxamide The procedure described in Example 2 was repeated, reacting 3-fluorophenyl isocyanate to give the pyrimidinecarboxamide as a pinkish powder, mp >250° (dec.) NMR (DMSO); 6.7–7.7$\delta$ multiplet, integral 4; 11.4$\delta$ singlet, 1; 12–13$\delta$, broad diffuse peak, 3. Mass Spectrum 281, 171, 111.

EXAMPLE 5

Preparation of N-(4-fluorophenyl)-1,2,3,4-tetrahydro-6-hydroxy-4-oxo-2-thioxo-5-pyrimidinecarboxamide 2-thiobarbituric acid (14.4 g) was suspended in pyridine and 4-fluorophenyl isocyanate (13.7 g) was added thereto. The reaction mixture was maintained at 90° C. for one hour, and thereafter left overnight at room temperature. The solids formed were collected, washed with pyridine, re-suspended in ethanol, and again collected and dried. A pale pink powder product was thereby obtained, mp >250° C. (dec.), NMR (DMSO) 7.0–7.7$\delta$ (multiplet, integral 4); 10.7–11.4$\delta$ (overlapping broad singlets, combined integral 4). MS, M/e 281 (Calc., 281).

EXAMPLE 6

Preparation of 1,2,3,4-tetrahydro-6-hydroxy-N-(4-methoxyphenyl)-4-oxo-2-thioxo-5-pyrimidinecarboxamide The procedure described in Example 2 was repeated, reacting 4-methoxyphenylisocyanate to give the pyrimidinecarboxamide as a yellow powder, mp >330° (dec.), NMR (DMSO) 3.81$\delta$ (singlet, integral 3); 6.9–7.6$\delta$ (two symmetrical near-doublets, 4); 11.4$\delta$ (singlet, 1); 11.7–12.3$\delta$, broad diffuse peak, 3. MS, 293, 171, 123.

EXAMPLE 7

Preparation of N-(4-ethoxyphenyl)-1,2,3,4-tetrahydro-6-hydroxy-4-oxo-2-thioxo-5-pyrimidinecarboxamide The procedure described in Example 2 was repeated, reacting 4-ethoxyphenylisocyanate to give the pyrimidine as a yellowish-pink powder, mp >250° (dec.), NMR (DMSO) 1.35$\delta$ (triplet, integral 3; 4.1$\delta$ (quartet, 2); 6.9≡7.6$\delta$ (two symmetrical near-doublets, 4); 11.4$\delta$ (singlet, 1); 12–13$\delta$, low broad diffuse peak. MS 307, 171, 137.

EXAMPLE 8

Preparation of N-(2-fluorophenyl)-1,2,3,4-tetrahydro-6-hydroxy-4-oxo-2-thioxo-5-pyrimidinecarboxamide The procedure described in Example 2 was repeated, reacting 2-fluorophenyl isocyanate to give the pyrimidine as a pale pinkish-purple powder, m.p. >250° (dec.). NMR (DMSO) 7.2–8.4$\delta$ (complex multiplets), 11.8$\delta$ (singlet). MS 281, 171, 111.

EXAMPLE 9

Preparation of N-(2,4-difluorophenyl)-1,2,3,4-tetrahydro-6-hydroxy-4-oxo-1-thioxo-5-pyrimidinecarboxamide The procedure described in Example 2 was repeated, reacting 2,4-difluorophenyl isocyanate to give the pyrimidine as a pale pinkish-purple powder, m.p. $\delta$250° (dec.). NMR (DMSO) 7.0–8.3$\delta$ (complex multiplet), 11.8$\delta$ (singlet); broad diffuse multiplet ca. 10.7–11.8$\delta$ MS, 299, 171, 129.

EXAMPLE 10

Preparation of 1,2,3,4-tethydro-6-hydroxy-N-(2-methoxy-5-methylphenyl)-4-oxo-2-thioxo-5-pyrimidinecarboxamide The procedure described in Example 2 was repeated, reacting 2-methoxy-5-methylphenyl isocyanate to give the pyrimidine as a pink powder, m.p. >280° (dec.). NMR (DMSO), 2.3$\delta$ (singlet, integral 3); 3.9$\delta$ (singlet, integral 3); 7.0$\delta$ (broad singlet, integral 2); 7.9$\delta$ (broad singlet, integral 1); 11.6$\delta$ (broad singlet, integral 1). MS 307, 171, 137.

Antitumor Activity Of The Compound Of Example 1

The spectrum of antitumor activity of the compound of Example 1 was determined employing a number of standard National Cancer Institute (NCI) protocols. The antitumor activity was determined in vivo against several different tumors, employing various treatment schedules and routes of administration. The results obtained, expressed in percent increases in life-span (% ILS) of the test animals, are summarized in the following table.

TABLE I

SUMMARY OF ANTITUMOR ACTIVITY OF COMPOUND OF EXAMPLE 1

| Tumor | Treatment Schedule[1] | Activity Rating[2] (% ILS, cures/total) |
|---|---|---|
| Murine tumors: | | |
| i.p. B16 melanoma | Days 1–9 | ++ (93,85) |
| s.c. CD8F$_1$ mammary tumor | Staging Day | — |
| s.c. Colon 38 tumor | Days 2–9 | — |

TABLE I-continued
SUMMARY OF ANTITUMOR ACTIVITY OF COMPOUND OF EXAMPLE 1

| Tumor | Treatment Schedule[1] | Activity Rating[2] (% ILS, cures/total) |
|---|---|---|
| i.p. L1210 leukemia | Days 1-9 | ++ (>275, 4/6; >229, 6/6) |
| s.c. L1210 leukemia | Days 1-9 | ++ (>200, 5/6; >154, 3/6) |
| i.c. L1210 leukemia | Days 1-9 | + (34,28) |
| i.v. Lewis lung carcinoma | Days 1-9 | — |
| i.p. M5076 sarcoma | Days 1-13 | ++ (72, 2/10; 72) |
| i.p. P388 leukemia | Days 1-5 | ++ (101,94) |
| Human tumor xenograft: | | |
| s.r.c. MX-1 mammary tumor | Days 1-9 | — |

[1]The test compound was administered i.p. (intraperitoneally) once a day on the days indicated, except in the case of the test for inhibition of the colon 38 tumor in which it was administered seven times per day, and the tests for inhibition of the M5076 sarcoma and MX-1 mammary tumors in which it was administered four times daily.
[2]Activity: ++ Reproduced activity: ≧50% ILS for i.p. and i.v. (intravenous) implanted tumors (≧75% ILS for P388), >90% inhibition of tumor growth for s.c. (subcutaneous) and s.r.c. (subrenal capsule), implanted tumors(≧100% inhibition for the staged CD8F$_1$ tumor).
+ Reproduced activity: 25-49% ILS for B16, L1210 and M5076, 20-74% ILS for P388, 40-49% ILS for Lewis lung, 58-89%, 80-89% and 80-99% inhibition of tumor growth for the colon 38, xenografts and the staged CD8F$_1$ mammary tumor, respectively.
— Inactive.

In both the i.p. and s.c. L1210 leukemia systems, a 100 mg/kg dose of the test compound administered i.p. daily for 9 days was curative in at least 50% of the test mice. The 100 mg/kg dose occasionally demonstrated some toxicity in the i.p. system. Employing a 50 mg/kg dose in these systems, maximum increased life spans of 87-190% were obtained.

Using the same treatment regimen (100 mg./kg. administered i.p. daily for 9 days), marginal activity (ILS=28-34%) was observed against the i.c. (intracranially) implanted L1210, indicative of a systemic rather than an i.c. effect.

In the B16 melanoma system, optimal ILS values of 93 and 85% were observed following daily i.p. treatment of 100 mg/kg for 9 days. Activity (ILS=25%) was observed over at least a 4-fold dosage range.

In three experiments involving the i.p. implanted M5076 sarcoma, maximum ILS values of 72, 72 and 48% were achieved after i.p. treatment on days 1, 5, 9 and 13.

The compound of Example 1 also demonstrated good activity in the standard NCI lymphocytic leukemia P388 preliminary screen, producing maximum ILS values of 101%, 94% and 62% following i.p. administration of a 50 mg/kg dose daily during a five day test.

The test compound was ineffective against the s.c. implanted CD8F$_1$ mammary and colon 38 carcinomas, the i.v. implanted Lewis lung carcinoma and the s.r.c. human MX-1 mammary carcinoma xenograft under the experimental conditions employed.

The data obtained in the various tests summarized above are tabulated in Table II below. The ratio of the survival time for the treated animals (T) to the survival time for the control animals (C) determined at varying dosages in the respective in vivo tests is set forth in the table:

TABLE II
IN VIVO TEST DATA FOR THE COMPOUND OF EXAMPLE 1

| NCI TEST PROTOCOL | DOSE mg/kg | TREATED/CONTROL PERCENT* | |
|---|---|---|---|
| 3B131 | 100 | 185 | 193 |
| (i.p.- | 50 | 152 | 169 |
| implanted | 25 | 137 | 158 |
| B 16 | 12 | 128 | |
| melanoma) | 6 | 108 | |
| 3CDJ2 | 900 | (—) | |
| (s.c.- | 450 | (—) | |
| implanted | 225 | (—) | |
| staged | 112 | 80 | |
| mammary | 56 | 61 | |
| adenocarcinoma | | | |
| CD8F1) | | | |
| 3C872 | 900 | (—) | |
| (s.c.- | 450 | (—) | |
| implanted | 225 | 51 | |
| colon 38 | 112 | (—) | 68 |
| carcinoma) | 56 | 70 | 120 |
| 3LE31 | | DATA SET FORTH IN | |
| (i.p.- | | TABLE III BELOW | |
| implanted | | | |
| L1210 | | | |
| leukemia) | | | |
| 3LE32 | 200 | (—) | (—) |
| (s.c.- | 100 | 300(5) | 254(3) |
| implanted | 50 | 140 | 127 |
| L1210 | 25 | 108 | 99 |
| leukemia) | 12.5 | 109 | 104 |
| 3LE37 | 200 | (—) | (—) |
| (i.c.- | 100 | 128 | 134 |
| implanted | 50 | 113 | 108 |
| L1210 | 25 | 98 | 98 |
| leukemia) | 12.5 | 94 | 106 |
| 3MBG5 | 600 | (—) | |
| (s.r.c. | 300 | (—) | |
| human | 150 | (—) | |
| mammary | 75 | 98 | |
| carcinoma | | | |
| MX-1 xenograft) | | | |
| 3M531 | 200 | (—) | (—) |
| (i.p.- | 100 | 148 | 172 |
| implanted | 50 | 124 | 147 |
| M5076 | 25 | 101 | 130 |
| sarcoma) | 12.5 | 117 | |
| 3PS31 | 200 | (—) | (—) |
| (i.p.- | 100 | (—) | (—) |
| implanted | 50 | 162 | 194 | 201 |
| P388 | 25 | | 145 | 138 |
| leukemia) | 12.5 | | | 120 |
| | 6.25 | | | 116 |
| | 3.13 | | | 110 |
| 3LL39 | 100 | 126 | |
| (i.v.- | 50 | 115 | |
| Lewis | 25 | 106 | |
| lung | 12.5 | 103 | |
| carcinoma) | | | |

*(#) = cures in test at specified dose
(—) = toxic dose
blank = no test

Effects Of Treatment Schedule And Route Of Administration On the Activity Of The Compound Of Example 1 Against s.c.-Implanted L-1210 Leukemia The influences of treatment schedule and route of administration on the antitumor activity of the compound of Example 1 were evaluated using the s.c. implanted L1210 leukemia system. The drug was tested in the form of a freeze dried dosage form containing 50 mg. of the compound and 100 mg. N-methylglucamine, reconstituted with 5 ml. of sterile water to yield a 10 mg/ml. solution at about pH 9.5.

The percentage increases in life span (%ILS) are shown in the accompanying drawing for different treatment regimens and routes of administration. As illustrated, increases in life span were noted using all treatments and routes of administration save for the i.p. and i.v. one day, one injection treatments (tests A and G in the drawing). The highest percent ILS was 471 obtained by daily i.p. injections of the active material on a five day schedule of 45 mg/kg/injection, corresponding to a total dose of 225 mg/kg/duration of the treatment (test C in the drawing). This dosage also gave 5 cures. Administration of the drug by oral injection daily for nine days also resulted in a high percent ILS of 452, employing a dosage of 124 mg/kg/injection, and a cumulative dose of 1116 mg/kg/duration of treatment (test I in the drawing). Use of this regimen resulted in 4 cures.

In the studies illustrated in the drawing toxicity was noted with the highest dose in each treatment schedule except for that involving i.p. administration every three hours on days one, five and nine of a nine day test (test F).

It may be seen that, under the experimental conditions utilized, substantial increases in life span (by definition, in excess of 25% ILS) were obtained utilizing each of the routes of administration and treatment schedules save for the single treatment i.p. and i.v. routes.

Comparison Of The Antitumor Activities Of A Variety Of Test Compounds In The Regression Of i.p.-Implanted Lymphoid Leukemia L1210

Samples of the test compounds of Examples 1–10 and a number of structurally-related control compounds were tested in accordance with National Cancer Institute test protocol 3LE31 (NCI Protocol 1.100, Cancer Chemotherapy Reports Part 3, Vol. 3, No. 2, September 1972) to determine the effects of the several compounds on i.p.-implanted L1210 leukemia (J. Nat'l. Cancer Inst. 13(5):1328, 1953). Each test involved implantation of the leukemia cells in six DBA/2 mice, one sex per experiment, the male mice weighing a minimum of 18 grams and the female mice weighing a minimum of 17 grams, and all of the test animals being within a three gram weight range. The test compound was administered by i.p. injections, in 0.1 ml. doses of diluted ascitic fluid ($10^5$ cells per dose), commencing one day after the tumor implant and continuing daily for nine days.

The test animals were weighed and survivors recorded on a regular basis during a thirty day test period. The ratio of survival time for the treated and control animals (T/C) was determined as a percentage.

The tests were carried out at varying dosage levels and with varying numbers of repetitions, depending upon the results obtained with each test compound. It has been statistically determined in the 3LE31 test system that an initial T/C value at least equal to 125% is necessary to demonstrate activity, while a reproducible T/C equal to or greater than 125% warrants further study. A reproducible T/C of 150% or higher is considered significant activity.

The number of mice "cured", viz., those surviving from each animal test group after the thirty day test period, is indicated in parenthesis following the T/C percentage data in Table III below:

TABLE III

Comparative Activities Against i.p. - Implanted L 1210 Leukemia
Test Compounds:

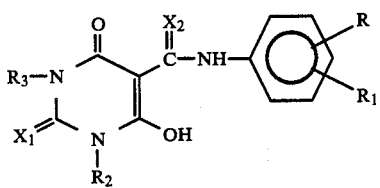

| Compound | R | $R_1$ | $R_2$ | $X_1$ | $X_2$ | $R_3$ | Dose (mg/kg) | T/C % | T/C % (Repeat) | T/C % (Repeat) | T/C % (Repeat) | T/C % (Repeat) |
|---|---|---|---|---|---|---|---|---|---|---|---|---|
| Example 1 | H | H | H | S | O | H | 100 | 375(4) | 139(2) | 133 | 91(1) | 337(4) |
| | | | | | | | 50 | 185 | 209 | 290 | 187 | 183 |
| | | | | | | | 25 | 116 | 132 | 144 | 124 | 134 |
| | | | | | | | 12.5 | 117 | 115 | 125 | | |
| | | | | | | | 6.25 | 116 | | | | |
| | | | | | | | 100 | | | 329(5) | 329(5) | 329(6) |
| | | | | | | | 50 | | | 142 | 175 | 164 |
| | | | | | | | 25 | | | 120 | 121 | 128 |
| | | | | | | | 12.5 | | | 112 | | |
| Example 2 | 2-Cl | H | H | S | O | H | 400 | | Toxic | | | |
| | | | | | | | 200 | 206(1) | 152 | | | |
| | | | | | | | 100 | 127 | 130 | | | |
| | | | | | | | 50 | 118 | 123 | | | |
| | | | | | | | 25 | 106 | | | | |
| Example 3 | 2-$CH_3$ | H | H | S | O | H | 200 | Toxic | Toxic | | | |
| | | | | | | | 100 | 135 | 164 | | | |
| | | | | | | | 50 | 112 | 130 | | | |
| | | | | | | | 25 | 108 | 119 | | | |
| Example 4 | 3-F | H | H | S | O | H | 200 | Toxic | 155 | | | |
| | | | | | | | 100 | 128 | | | | |
| | | | | | | | 50 | 114 | 113 | | | |
| | | | | | | | 25 | 114 | 106 | | | |
| Example 5 | 4-F | H | H | S | O | H | 200 | Toxic | | | | |
| | | | | | | | 100 | 133 | | | | |
| | | | | | | | 50 | 112 | | | | |
| | | | | | | | 25 | 111 | | | | |

TABLE III-continued
Comparative Activities Against i.p. - Implanted L 1210 Leukemia
Test Compounds:

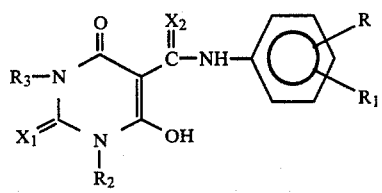

| Compound | R | $R_1$ | $R_2$ | $X_1$ | $X_2$ | $R_3$ | Dose (mg/kg) | T/C % | T/C % (Repeat) | T/C % (Repeat) | T/C % (Repeat) | T/C % (Repeat) |
|---|---|---|---|---|---|---|---|---|---|---|---|---|
| Example 6 | 4-OCH$_3$ | H | H | S | O | H | 400 | | 127 | | | |
| | | | | | | | 200 | 127 | 107 | | | |
| | | | | | | | 100 | 104 | 105 | | | |
| | | | | | | | 50 | 108 | 106 | | | |
| | | | | | | | 25 | 112 | 105 | | | |
| Example 7 | 4-OC$_2$H$_5$ | H | H | S | O | H | 200 | Toxic | | | | |
| | | | | | | | 100 | Toxic | 178 | | | |
| | | | | | | | 50 | 129 | 105 | | | |
| | | | | | | | 25 | 115 | 98 | | | |
| | | | | | | | 12.5 | | 97 | | | |
| | | | | | | | 6.25 | | 102 | | | |
| Example 8 (triethanol-amine salt) | 2-F | H | H | S | O | H | 200 | 118 | | | | |
| | | | | | | | 100 | 128 | | | | |
| | | | | | | | 50 | 105 | | | | |
| | | | | | | | 25 | 148 | | | | |
| Example 9 | 2-F | 4-F | H | S | O | H | 200 | 133 | | | | |
| | | | | | | | 100 | 114 | | | | |
| | | | | | | | 50 | 113 | | | | |
| | | | | | | | 25 | 113 | | | | |
| Example 10 (triethyl-amine salt) | 2-OCH$_3$ | 5-CH$_3$ | H | S | O | H | 200 | 113 | | | | |
| | | | | | | | 100 | 113 | | | | |
| | | | | | | | 50 | 130 | | | | |
| | | | | | | | 25 | 110 | | | | |
| Control A | 4-Cl | H | H | S | O | H | 200 | Toxic | Toxic | | | |
| | | | | | | | 100 | 125 | 120 | 111 | | |
| | | | | | | | 50 | 121 | 109 | 102 | | |
| | | | | | | | 25 | 110 | 103 | 103 | | |
| Control B | H | H | H | O | O | H | 200 | 137 | 134(2) | 166 | | |
| | | | | | | | 100 | 149 | 179 | 142 | | |
| | | | | | | | 50 | 124 | 134 | 112 | | |
| | | | | | | | 25 | 118 | 115 | 108 | | |
| Control C (triethylamine salt) | H | H | H | O | O | H | 400 | | 233 | | | |
| | | | | | | | 200 | 211 | 179 | | | |
| | | | | | | | 100 | 143 | 114 | | | |
| | | | | | | | 50 | 108 | 112 | | | |
| | | | | | | | 25 | 108 | 112 | | | |
| Control D | 2-CH$_3$ | H | H | O | O | H | 200 | 124 | | | | |
| | | | | | | | 100 | 106 | | | | |
| | | | | | | | 50 | 104 | | | | |
| | | | | | | | 25 | 108 | | | | |
| Control F | 4-OCH$_3$ | H | H | O | O | H | 200 | 117 | | | | |
| | | | | | | | 100 | 105 | | | | |
| | | | | | | | 50 | 105 | | | | |
| | | | | | | | 25 | 109 | | | | |
| Control F | 4-OC$_2$H$_5$ | H | H | O | O | H | 200 | 115 | | | | |
| | | | | | | | 100 | 115 | | | | |
| | | | | | | | 50 | 110 | | | | |
| | | | | | | | 25 | 110 | | | | |
| Control G | H | H | H | S | O | CH$_3$ | 200 | Toxic | | | | |
| | | | | | | | 100 | 87 | | | | |
| | | | | | | | 50 | 98 | | | | |
| | | | | | | | 25 | 94 | | | | |
| Control H (triethylamine salt) | H | H | H | S | O | CH$_3$ | 200 | Toxic | | | | |
| | | | | | | | 100 | Toxic | | | | |
| | | | | | | | 50 | Toxic | | | | |
| | | | | | | | 25 | Toxic | | | | |
| | | | | | | | 12.5 | 98 | | | | |
| | | | | | | | 6.25 | 98 | | | | |
| | | | | | | | 3.12 | 98 | | | | |
| | | | | | | | 1.56 | 97 | | | | |
| Control I | 3-NO$_2$ | H | H | S | O | CH$_3$ | 200 | 112 | | | | |
| | | | | | | | 100 | 102 | | | | |
| | | | | | | | 50 | 98 | | | | |
| | | | | | | | 25 | 102 | | | | |
| Control J (triethylamine salt) | 3-NO$_2$ | H | H | S | O | CH$_3$ | 200 | 101 | | | | |
| | | | | | | | 100 | 104 | | | | |
| | | | | | | | 50 | 94 | | | | |

TABLE III-continued
Comparative Activities Against i.p. - Implanted L 1210 Leukemia
Test Compounds:

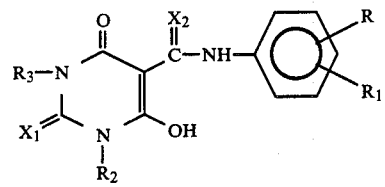

| Compound | R | $R_1$ | $R_2$ | $X_1$ | $X_2$ | $R_3$ | Dose (mg/kg) | T/C % | T/C % (Repeat) | T/C % (Repeat) | T/C % (Repeat) | T/C % (Repeat) |
|---|---|---|---|---|---|---|---|---|---|---|---|---|
| Control K | H | H | $CH_3$ | S | O | $CH_3$ | 25 | 100 | | | | |
| | | | | | | | 200 | Toxic | | | | |
| | | | | | | | 100 | 121 | | | | |
| | | | | | | | 50 | 109 | | | | |
| | | | | | | | 25 | 107 | | | | |
| Control L (triethylamine salt) | H | H | $CH_3$ | S | O | $CH_3$ | 200 | Toxic | | | | |
| | | | | | | | 100 | Toxic | | | | |
| | | | | | | | 50 | Toxic | | | | |
| | | | | | | | 25 | 108 | | | | |
| Control M (triethylamine salt) | 4-Cl | H | $CH_3$ | S | O | $CH_3$ | 200 | Toxic | | | | |
| | | | | | | | 100 | Toxic | | | | |
| | | | | | | | 50 | Toxic | | | | |
| | | | | | | | 25 | Toxic | | | | |
| | | | | | | | 12 | 106 | | | | |
| | | | | | | | 6 | 95 | | | | |
| | | | | | | | 3 | 92 | | | | |
| | | | | | | | 1.5 | 106 | | | | |
| | | | | | | | .75 | 102 | | | | |
| Control N (triethylamine salt) | 2-$CH_3$ | 5-$CH_3$ | $CH_3$ | S | O | $CH_3$ | 200 | Toxic | | | | |
| | | | | | | | 100 | Toxic | | | | |
| | | | | | | | 50 | Toxic | | | | |
| | | | | | | | 25 | 103 | | | | |
| Control O | H | H | H | S | O | phenyl | 200 | Toxic | | | | |
| | | | | | | | 100 | 123 | | | | |
| | | | | | | | 50 | 115 | | | | |
| | | | | | | | 25 | 104 | | | | |
| Control P (dimethyl-ethanol-amine salt) | H | H | H | S | O | phenyl | 200 | Toxic | | | | |
| | | | | | | | 100 | Toxic | | | | |
| | | | | | | | 50 | 116 | | | | |
| | | | | | | | 25 | 110 | | | | |
| Control Q | 4-Cl | H | H | S | O | phenyl | 200 | Toxic | | | | |
| | | | | | | | 100 | 112 | | | | |
| | | | | | | | 50 | 92 | | | | |
| | | | | | | | 25 | 100 | | | | |
| Control R (triethylamine salt) | 4-Cl | H | H | S | O | phenyl | 200 | Toxic | | | | |
| | | | | | | | 100 | 88 | | | | |
| | | | | | | | 50 | 121 | | | | |
| | | | | | | | 25 | 106 | | | | |
| Control S | H | H | phenyl | S | O | phenyl | 400 | | Toxic | 133 | 133 | |
| | | | | | | | 200 | 123 | 128 | 103 | 103 | |
| | | | | | | | 100 | 100 | 92 | 87 | 87 | |
| | | | | | | | 50 | 100 | | | | |
| | | | | | | | 25 | 97 | | | | |
| Control T (triethylamine salt) | H | H | phenyl | S | O | phenyl | 400 | | 109 | | | |
| | | | | | | | 200 | 121 | 100 | | | |
| | | | | | | | 100 | 109 | 92 | | | |
| | | | | | | | 50 | 109 | | | | |
| | | | | | | | 25 | 102 | | | | |
| Control U (triethyl-amine salt) | 2-i-$C_3H_7$ | 6-i-$C_3H_7$ | phenyl | S | O | phenyl | 200 | 112 | | | | |
| | | | | | | | 100 | 104 | | | | |
| | | | | | | | 50 | 100 | | | | |
| | | | | | | | 25 | 101 | | | | |

TABLE III-continued
Comparative Activities Against i.p. - Implanted L 1210 Leukemia
Test Compounds:

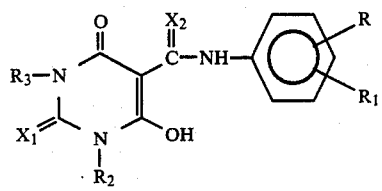

| Compound | R | $R_1$ | $R_2$ | $X_1$ | $X_2$ | $R_3$ | Dose (mg/kg) | T/C % | T/C % (Repeat) | T/C % (Repeat) | T/C % (Repeat) | T/C % (Repeat) |
|---|---|---|---|---|---|---|---|---|---|---|---|---|
| Control V | 2-COOCH$_3$ | H | phenyl | S | O | phenyl | 200 | Toxic | | | | |
| | | | | | | | 100 | Toxic | | | | |
| | | | | | | | 50 | 106 | | | | |
| | | | | | | | 25 | 102 | | | | |
| Control W | H | H | H | S | S | H | 200 | 103 | | | | |
| | | | | | | | 100 | 94 | | | | |
| | | | | | | | 50 | 102 | | | | |
| | | | | | | | 25 | 101 | | | | |
| Control X | H | H | H | O | S | H | 200 | 104 | | | | |
| | | | | | | | 100 | 97 | | | | |
| | | | | | | | 50 | 98 | | | | |
| | | | | | | | 25 | 105 | | | | |

As may be seen from Table III, the compound of Example 1 exhibited significant activity in the i.p.-implanted lymphoid leukemia test at dosage levels of both 50 mg/kg. and 100 mg/kg., and produced a number of cures at 100 mg/kg. With the exception of the compound of Example 5, the materials of the other examples similarly exhibited significant activity in the test. On the other hand, only two control compounds, the barbituric acid derivatives of Controls B and C, exhibited significant activity in the test. The compound of Control A, previously believed to exhibit moderate activity in the 3LE31 test protocol, was found upon further testing to exhibit a T/C less than 125% and thus to be inactive.

From the preceding, it will be seen that, in accordance with the present invention, a class of novel 5-pyrimidinecarboxamides is provided, the members of which exhibit substantial cytotoxic activity and induce regression and/or inhibit growth of leukemia and various malignant tumors in mammals. It will be apparent that various changes may be made in the method of preparation and use, as well as in the particular substitution, of the therapeutically active compounds of the invention. Accordingly, the preceding disclosure should be construed as illustrative only, and the scope of the invention should be interpreted in accordance with the claims appended hereto.

We claim:

1. A compound of the formula

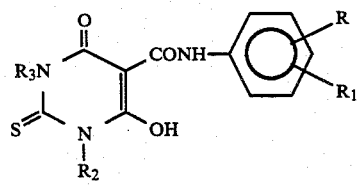

wherein:

R is hydrogen, 2- or 3-halo, 2-methyl, 4-fluoro, 2- or 4-alkoxy having from 1 to 6 carbon atoms, 2 or 4-trifluoromethyl, and $R_1$ is hydrogen; or R is 2-fluoro and $R_1$ is 4-fluoro; or R is 2-methoxy and $R_1$ is 5-methyl; and $R_2$ and $R_3$ are hydrogen atoms or carbohydrate residues selected from the group consisting of furanosyl, pyranosyl, gluocopyranosyl or galactopyranosyl groups, their deoxy derivatives, and hydroxyalkoxyalkyl and polyhydroxyalkyl groups having from 2–12 carbon atoms in each of the alkoxy and alkyl moieties thereof; and, with the exception of the compound wherein R is 4-methoxy and $R_1$ is hydrogen, the pharmacologically acceptable acid-addition salts thereof.

2. The compound of claim 1, wherein R is hydrogen or a 2-chloro, 2-methyl, 3-fluoro, 4-fluoro, 4-methoxy or 4-ethoxy group.

3. The compound of claim 1, namely 1,2,3,4-tetrahydro-6-hydroxy-4-oxo-N-phenyl-2-thioxo-5-pyrimidinecarboxamide.

4. The compound of claim 1, namely N-(2-chlorophenyl)-1,2,3,4-tetrahydro-6-hydroxy-4-oxo-2-thioxo-5-pyrimidinecarboxamide.

5. The compound of claim 1, namely 1,2,3,4-tetrahydro-6-hydroxy-N-(2-methylphenyl)-4-oxo-2-thioxo-5-pyrimidinecarboxamide.

6. The compound of claim 1, namely N-(3-fluorophenyl)-1,2,3,4-tetrahydro-6-hydroxy-4-oxo-2-thioxo-5-pyrimidinecarboxamide.

7. The compound of claim 1, namely 1,2,3,4-tetrahydro-6-hydroxy-N-(4-methoxyphenyl)-4-oxo-2-thioxo-5-pyrimidinecarboxamide.

8. The compound of claim 1, namely N-(4-ethoxyphenyl)-1,2,3,4-tetrahydro-6-hydroxy-4-oxo-2-thioxo-5-pyrimidinecarboxamide.

9. The compound of claim 1, namely N-(2-fluorophenyl)-1,2,3,4-tetrahydro-6-hydroxy-4-oxo-2-thioxo-5-pyrimidinecarboxamide.

10. The compound of claim 1, namely N-(2,4-difluorophenyl)-1,2,3,4-tetrahydro-6-hydroxy-4-oxo-2-thioxo-5-pyrimidinecarboxamide.

11. The compound of claim 1, namely 1,2,3,4-tetrahydro-6-hydroxy-N-(2-methoxy-5-methylphenyl)-4-oxo-2-thioxo-5-pyrmidinecarboxamide.

12. A method for inducing regression of leukemia and inhibition of the growth of tumors in mammals, which comprises administering an effective amount of the compound of claim 1 to mammals.

13. The method of claim 12, which comprises administering an effective amount of the compound wherein R is hydrogen or a 2-chloro, 2-methyl, 2-, 3- or 4-fluoro, 2- or 4-methoxy or 4-ethoxy group.

14. The method of claim 12, which comprises administering an effective amount of 1,2,3,4-tetrahydro-6-hydroxy-4-oxo-N-phenyl-2-thioxo-5-pyrimidinecarboxamide.

15. The method of claim 12, which comprises administering an effective amount of N-(2-chlorophenyl)-1,2,3,4-tetrahydro-6-hydroxy-4-oxo-2-thioxo-5-pyrimidinecarboxamide.

16. The method of claim 12, which comprises administering an effective amount of 1,2,3,4-tetrahydro-6-hydroxy-N-(2-methylphenyl)-4-oxo-2-thioxo-5-pyrimidinecarboxamide.

17. The method of claim 12, which comprises administering an effective amount of N-(3-fluorophenyl-1,2,3,4-tetrahydro-6-hydroxy-4-oxo-2-thioxo-5-pyrimidinecarboxamide.

18. The method of claim 12, which comprises administering an effective amount of 1,2,3,4-tetrahydro-6-hydroxy-N-(4-methoxyphenyl)-4-oxo-2-thioxo-5-pyrimidinecarboxamide.

19. The method of claim 12, which comprises administering an effective amount of N-(4-ethoxyphenyl)-1,2,3,4-tetrahydro-6-hydroxy-4-oxo-2-thioxo-5-pyrimidinecarboxamide.

20. The method of claim 12, which comprises administering an effective amount of N-(2-fluorophenyl)-1,2,3,4-tetrahydro-6-hydroxy-4-oxo-2-thioxo-5-pyrimidinecarboxamide.

21. The method of claim 12, which comprises administering an effective amount of N-(2,4,-difluorophenyl)-1,2,3,4-tetrahydro-6-hydroxy-4-oxo-2-thioxo-5-pyrimidinecarboxamide.

22. The method of claim 12, which comprises administering an effective amount of 1,2,3,4-tetrahydro-6-hydroxy-N-(2-methoxy-5-methylphenyl)-4-oxo-2-thioxo-5-pyrimidinecarboxamide.

23. A pharmaceutical composition for inducing regression of leukemia and inhibition of the growth of tumors in mammals, which comprises a therapeutically effective amount of the compound of claim 1 in admixture with a pharmaceutically acceptable, substantially nontoxic carrier or excipient.

24. The composition of claim 23, comprising a therapeutically effective amount of the compound wherein R is hydrogen or a 2-chloro, 2-methyl, 2-, 3- or 4-fluoro, 2- or 4-methoxy or 4-ethoxy group.

* * * * *